(12) United States Patent
Amano (10) Patent No.: US 8,019,126 B2
(45) Date of Patent: Sep. 13, 2011

(54) BIOMETRIC DATA ACQUISITION DEVICE, BIOMETRIC DATA ACQUISITION METHOD AND BIOMETRIC AUTHENTICATION DEVICE

(75) Inventor: Kazuhiko Amano, Tokyo (JP)

(73) Assignee: Seiko Epson Corporation, Tokyo (JP)

( * ) Notice: Subject to any disclaimer, the term of this patent is extended or adjusted under 35 U.S.C. 154(b) by 1036 days.

(21) Appl. No.: 11/740,004

(22) Filed: Apr. 25, 2007

(65) Prior Publication Data

US 2007/0253602 A1 Nov. 1, 2007

(30) Foreign Application Priority Data

Apr. 27, 2006 (JP) ................................. 2006-123403
Mar. 20, 2007 (JP) ................................. 2007-072616

(51) Int. Cl.
*G06K 9/00* (2006.01)

(52) U.S. Cl. ....... 382/115; 340/5.52; 340/5.83; 713/186

(58) Field of Classification Search .................. 382/235, 382/340, 704, 902, 115–127; 340/5.53, 5.1, 340/5.2, 5.52, 5.8–5.86; 600/162, 476; 356/71; 713/186; 902/3
See application file for complete search history.

(56) References Cited

U.S. PATENT DOCUMENTS

| | | | | |
|---|---|---|---|---|
| 5,719,950 | A * | 2/1998 | Osten et al. ..................... | 382/115 |
| 5,787,185 | A * | 7/1998 | Clayden ......................... | 382/115 |
| 6,301,375 | B1 * | 10/2001 | Choi .............................. | 382/115 |
| 2003/0046228 | A1 * | 3/2003 | Berney ........................... | 705/41 |

FOREIGN PATENT DOCUMENTS

| | | | |
|---|---|---|---|
| EP | 0996284 A1 * | 4/2000 | |
| JP | A 06-223163 | 8/1994 | |
| JP | A 2004-56257 | 2/2004 | |
| JP | B2 3549795 | 8/2004 | |

OTHER PUBLICATIONS

Watanabe et al., "Implementation of high-speed face recognition system that uses an optical parallel correlator." Feb. 10, 2005, Applied Optics, vol. 44 No. 5, p. 666-676.*

* cited by examiner

*Primary Examiner* — Aaron Carter
(74) *Attorney, Agent, or Firm* — Oliff & Berridge, PLC (57) ABSTRACT

A biometric data acquisition device for acquiring data of a living body by irradiating the living body with light includes: a light source unit that emits light to the living body; a plurality of light receiving elements that receive transmitted light or reflected light, which is transmitted through the living body or reflects from the living body, respectively, by irradiating the living body with the light from the light source unit; an openable and closable gate provided for each of the plurality of light receiving elements; and an opening and closing control unit that controls opening and closing of the gate so as to make uniform intensities of light received by the plurality of light receiving elements.

19 Claims, 6 Drawing Sheets

BIOMETRIC DATA ACQUISITION DEVICE, BIOMETRIC DATA ACQUISITION METHOD AND BIOMETRIC AUTHENTICATION DEVICE

BACKGROUND OF THE INVENTION

1. Technical Field

Several aspects of the present invention relate to a biometric data acquisition device, a biometric data acquisition method and a biometric authentication device for utilizing biometric data.

2. Related Art

Recently, biometric authentication utilizing biometric data such as the fingerprint, iris and vein pattern of a legitimate user is performed for authentication of the legitimate user (see Japanese Patent No. 3,549,795, for example).

To perform biometric authentication, various biometric data acquisition devices are used.

Among such biometric data acquisition devices, ones including a light source unit that emits light and a light receiving element that receives light are known.

A living body is irradiated with light from the light source unit, and the light from the living body is received.

The received light is converted to an electrical signal, allowing biometric data to be obtained.

Today, devices require authentication such as potable devices and personal computers overflow in the environment.

In such circumstances, bulky biometric data acquisition devices requiring higher power consumption are being avoided.

On the other hand, due to increasing security awareness, as increasingly high accuracy of authentication is demanded, improvement of accuracy of biometric data is also needed.

However, if a biometric data acquisition device is reduced in size, the dynamic range of illuminating light is also reduced.

This reduction limits the scope of applications.

Therefore, there is a problem that the obtained biometric data has reduced quality.

SUMMARY

An advantage of several aspects of the present invention is to obtain biometric data with high accuracy and further provide a biometric data acquisition device, a biometric data acquisition method and a biometric authentication device that easily allow reduced size.

A biometric data acquisition device according to a first aspect of the invention is one for acquiring data of a living body by irradiating the living body with light.

The biometric data acquisition device includes: a light source unit that emits light to the living body; a plurality of light receiving elements that receive transmitted light or reflected light, which is transmitted through the living body or reflects from the living body, respectively, by irradiating the living body with the light from the light source unit; an openable and closable gate provided for each of the plurality of light receiving elements; and an opening and closing control unit that controls opening and closing of the gate so as to make uniform intensities of light received by the plurality of light receiving elements.

In the biometric data acquisition device according to this aspect of the invention, intensities of light received by the plurality of light receiving elements can be made uniform, and therefore the light intensities can be equalized over the plurality of light receiving elements without depending on the distances from the light source unit.

Thus, quality of biometric data can be improved while the dynamic range is being decreased.

Preferably, in the biometric data acquisition device according to the first aspect of the invention, the opening and closing control unit sets a time to open a gate corresponding to one of the plurality of light receiving elements arranged in a position remote from the light source unit in accordance with a time at which an intensity of light emitted from the light source unit is high.

The opening and closing control unit also sets a time to open a gate corresponding to one of the plurality of light receiving elements arranged in a position near to the light source unit in accordance with a time at which the intensity is low.

Preferably, in the biometric data acquisition device according to the first aspect of the invention, the opening and closing control unit sets a time to open a gate corresponding to one of the light receiving elements arranged in a position remotest from the light source unit in accordance with a time at which an intensity of light emitted from the light source unit is at a peak.

As, starting from the one of the light receiving elements arranged in a position remotest from the light source unit, each light receiving element is nearer to the light source unit, a time to open the gate is subsequently shifted in accordance with decay of the light intensity.

Preferably, in the biometric data acquisition device according to the first aspect of the invention, the opening and closing control unit makes long a time period during which a gate corresponding to one of the plurality of light receiving elements arranged in a position remote from the light source unit is opened, and makes short a time period during which a gate corresponding to one of the plurality of light receiving elements arranged in a position near to the light source unit is opened.

In the biometric data acquisition device according to this aspect of the invention, improvement of quality of biometric data can be ensured.

Preferably, the biometric data acquisition device according to the first aspect of the invention is wearable on a body.

In the biometric data acquisition device according to this aspect of the invention, biometric data can be used in various situations.

Thus, the convenience can be enhanced.

A biometric data acquisition method according to a second aspect of the invention is one for acquiring data of a living body by irradiating the living body with light.

The biometric data acquisition method includes: irradiating the living body with light emitted from a light source unit; receiving by a plurality of light receiving elements transmitted light or reflected light, which is transmitted through the living body or reflects from the living body, respectively, by irradiating the living body with the light from the light source unit; and making uniform intensities of light received by the plurality of light receiving elements by an opening and closing control unit that controls opening and closing of a gate provided for the plurality of light receiving elements.

In the biometric data acquisition method according to this aspect of the invention, intensities of light received by the plurality of light receiving elements can be made uniform, and therefore the light intensities can be equalized over the plurality of light receiving elements without depending on the distances from the light source unit.

Thus, quality of biometric data can be improved while the dynamic range is being decreased.

A biometric authentication device according to a third aspect of the invention includes: a biometric data acquisition unit for acquiring data of a living body by irradiating the living body with light; and an authentication unit for performing personal authentication with the data of the living body acquired by the biometric data acquisition unit.

The biometric data acquisition unit includes: a light source unit that emits light to the living body; a plurality of light receiving elements that receive transmitted light or reflected light, which is transmitted through the living body or reflects from the living body, respectively, by irradiating the living body with the light from the light source unit; an openable and closable gate provided for each of the plurality of light receiving elements; and an opening and closing control unit that controls opening and closing of the gate so as to make uniform intensities of light received by the plurality of light receiving elements.

The authentication unit includes: a biometric data storing unit that stores in advance data of the living body acquired by the biometric data acquisition unit; and an authentication control unit that compares the data of the living body stored in advance in the biometric data storing unit with the data of the living body acquired in authentication by the biometric data acquisition unit, and if both the stored data and the acquired data match, outputs a permission signal representing completion of authentication.

In the biometric authentication device according to this aspect of the invention, intensities of light received by the plurality of light receiving elements can be made uniform, and therefore the light intensities can be equalized over the plurality of light receiving elements without depending on the distances from the light source unit.

Thus, quality of biometric data can be improved while the dynamic range is being decreased.

As a result, higher accuracy of authentication can be easily achieved.

Preferably, the biometric authentication device according to the third aspect of the invention is wearable on a body.

In the biometric authentication device according to this aspect of the invention, biometric authentication can be performed in various situations.

Thus, the convenience can be enhanced.

A biometric authentication device according to a fourth aspect of the invention includes: a biometric data acquisition unit for acquiring data of a living body by irradiating the living body with light; and an authentication unit for performing personal authentication with the data of the living body acquired by the biometric data acquisition unit.

The biometric authentication device is coupled to an external device, and is designed to be wearable on a body.

The biometric data acquisition unit includes: a light source unit that emits light to the living body; a plurality of light receiving elements that receive transmitted light or reflected light, which is transmitted through the living body or reflects from the living body, respectively, by irradiating the living body with the light from the light source unit; an openable and closable gate provided for each of the plurality of light receiving elements; and an opening and closing control unit that controls opening and closing of the gate so as to make uniform intensities of light received by the plurality of light receiving elements.

The authentication unit includes: a biometric data storing unit that stores in advance data of the living body acquired by the biometric data acquisition unit; an identification data storing unit that stores identification data of an individual; an authentication control unit that compares the data of the living body stored in advance in the biometric data storing unit with the data of the living body acquired in authentication by the biometric data acquisition unit, and if both the stored data and the acquired data match, outputs a permission signal representing completion of authentication; an authentication holding unit that holds authentication completion information indicating a state of completed authentication; a release unit that releases a state of the authentication completion information held by the authentication holding unit when detecting the biometric authentication device is removed from the body; and a sending unit that sends identification data stored in the identification data storing unit to the external device when a permission signal output from the authentication control unit is input.

In the biometric authentication device according to this aspect of the invention, intensities of light received by the plurality of light receiving elements can be made uniform, and therefore the light intensities can be equalized over the plurality of light receiving elements without depending on the distances from the light source unit.

Thus, quality of biometric data can be improved while the dynamic range is being decreased.

As a result, higher accuracy of authentication can be easily achieved.

The authentication completion information is held until the device is removed from a body, and therefore authentication needs not be performed in each time as long as the biometric authentication device 1 is worn, allowing quick responses.

When the device is removed from a body, a state of holding authentication completion information is released.

This allows improvement of security.

Further, since identification data of an individual is sent, various controls can be performed by an external device coupled to the device.

A biometric authentication device according to a fifth aspect of the invention comprises: a biometric data acquisition unit for acquiring data of a living body by irradiating the living body with light; and an authentication unit for performing personal authentication with the data of the living body acquired by the biometric data acquisition unit.

The biometric data acquisition unit includes: a light source unit that emits light to the living body; a plurality of light receiving elements receiving transmitted light or reflected light, which is transmitted through the living body or reflects from the living body, respectively, by irradiating the living body with the light from the light source unit; an openable and closable gate provided for each of the plurality of light receiving elements; and an opening and closing control unit that controls opening and closing of the gate so as to make uniform intensities of light received by the plurality of light receiving elements.

The authentication unit includes: a resting state detection unit that detects a resting state of the living body; a biometric data storing unit that stores in advance a vein pattern of the living body acquired by the biometric data acquisition unit; an authentication control unit that compares the vein pattern stored in advance in the biometric data storing unit with the vein pattern acquired in authentication by the biometric data acquisition unit, and if both the stored vein pattern and the acquired vein pattern match, outputs a permission signal representing completion of authentication; and an authentication prohibition control unit that prohibits authentication by the authentication control unit if a result detected by the resting state detection unit exceeds a predetermined threshold value.

A biometric data acquisition device according to a sixth aspect of the invention is one for acquiring data of a living body by irradiating the living body with light.

The biometric data acquisition device comprises: a light source unit that emits light to the living body; a plurality of light receiving elements that receive transmitted light or reflected light, which is transmitted through the living body or reflects from the living body, respectively, by irradiating the living body with the light from the light source unit; and a plurality of openable and closable gates.

The plurality of gates are each provided for one of the plurality of light receiving elements.

At least two of the plurality of gates are opened at a different timing after starting irradiation of the living body with the light.

A biometric data acquisition device according to a seventh aspect of the invention is one for acquiring data of a living body by irradiating the living body with light.

The biometric data acquisition device comprises: a light source unit that emits light to the living body; a plurality of light receiving elements that receive transmitted light or reflected light, which is transmitted through the living body or reflects from the living body, respectively, by irradiating the living body with the light from the light source unit; and a plurality of openable and closable gates.

The plurality of gates are each provided for one of the plurality of light receiving elements.

At least two of the plurality of gates are closed at a different timing, after the at least two gates have been opened.

In the above-mentioned biometric authentication device, the intensity of the light may vary with time.

In the biometric authentication device according to this aspect of the invention, as described above, quality of biometric data can be improved while the dynamic range is being decreased.

As a result, higher accuracy of authentication can be easily achieved,

Since authentication is not performed unless a living body is in a resting state, accuracy of authentication can be improved.

According to some aspects of the invention, the dynamic range can be reduced, or quality of biometric data can be improved.

Further, it is possible to omit optical elements such as a filter for adjusting the intensity of irradiation light, and therefore the entire size of a device can be easily reduced.

BRIEF DESCRIPTION OF THE DRAWINGS

The invention will be described with reference to the accompanying drawings, wherein like numbers reference like elements.

FIGS. 5A, 5B and 5C show a modification of FIGS. 4A, 4B and 4C.

DESCRIPTION OF EXEMPLARY EMBODIMENTS

First Embodiment

A biometric authentication device in a first embodiment of the invention will be described below referring to figures.

Figure 1:
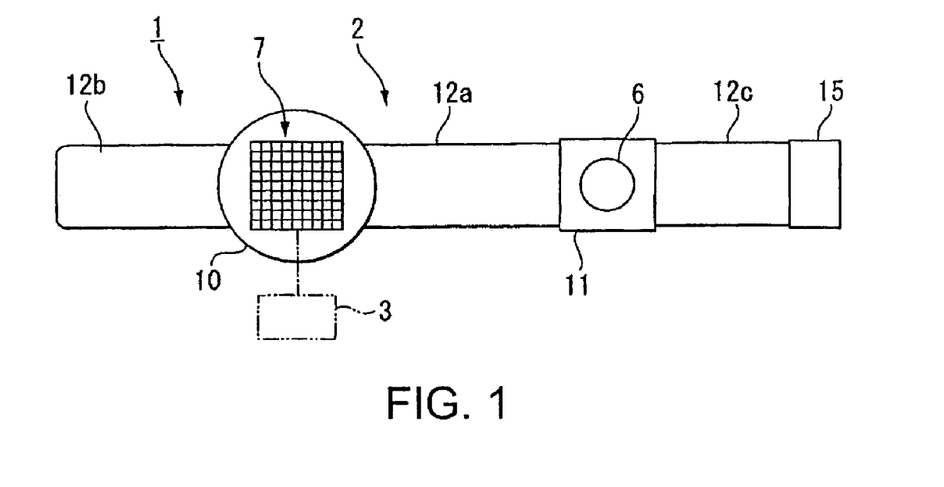
FIG. 1 is a plan view showing a first embodiment of a biometric authentication device according to the invention.

FIG. 1 shows a biometric authentication device 1 as an embodiment of the invention.

The biometric authentication device 1 includes a circular base unit 10 formed in a circular plate shape and a rectangular base unit 11 formed in a rectangular shape.

The circular base unit 10 and the rectangular base unit 11 are coupled to each other with a band unit 12a provided therebetween.

The circular base unit 10 is provided with a band unit 12b extending in the opposite direction to the band unit 12a, and the rectangular base unit 11 is provided with a band unit 12c extending in the opposite direction to the band unit 12a.

Provided at the edge of the band unit 12c is a latch unit 15 for latching with the edge of the band unit 12b.

Figure 2:
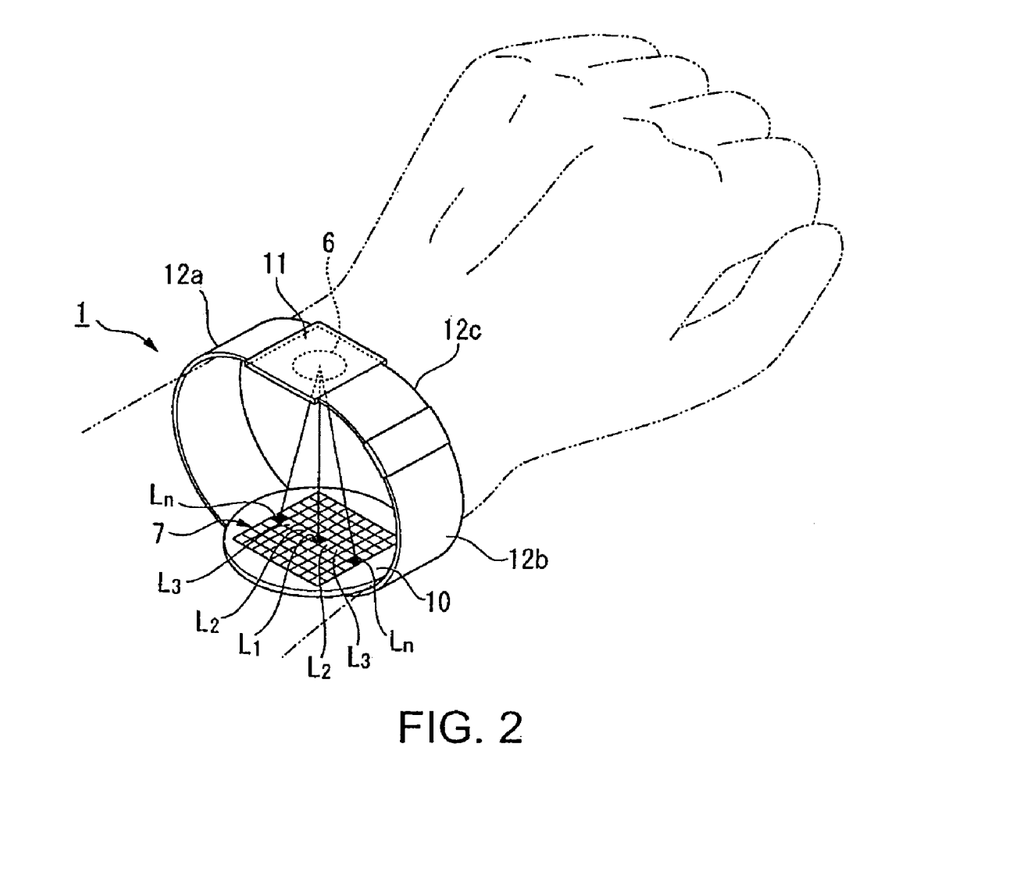
FIG. 2 is an explanatory view showing a state of the biometric authentication device of FIG. 1 worn around a wrist.

In such a configuration, as shown in FIG. 2, the band units 12a, 12b and 12c are wounded around a wrist and the latch unit 15 latches with the edge of the band unit 12b, permitting the biometric authentication device 1 to be worn around the wrist.

The biometric authentication device 1, as shown in FIG. 1, includes biometric data acquisition unit (biometric data acquisition device) 2 for acquiring a vein pattern of a living body, and an authentication unit 3 for performing personal authentication using the vein pattern acquired by the biometric data acquisition unit 2.

The biometric data acquisition unit 2 includes a point light source unit (light source unit) 6 that emits illuminating light, and a light receiving unit 7 that receives light.

The point light source unit 6 is, for example, made of a light emitting diode (LED), and is provided on one main surface of the rectangular base unit 11.

The light receiving unit 7 is, for example, made of a charge-coupled device (CCD), and is provided on one main surface of the circular base unit 10.

Figure 3:
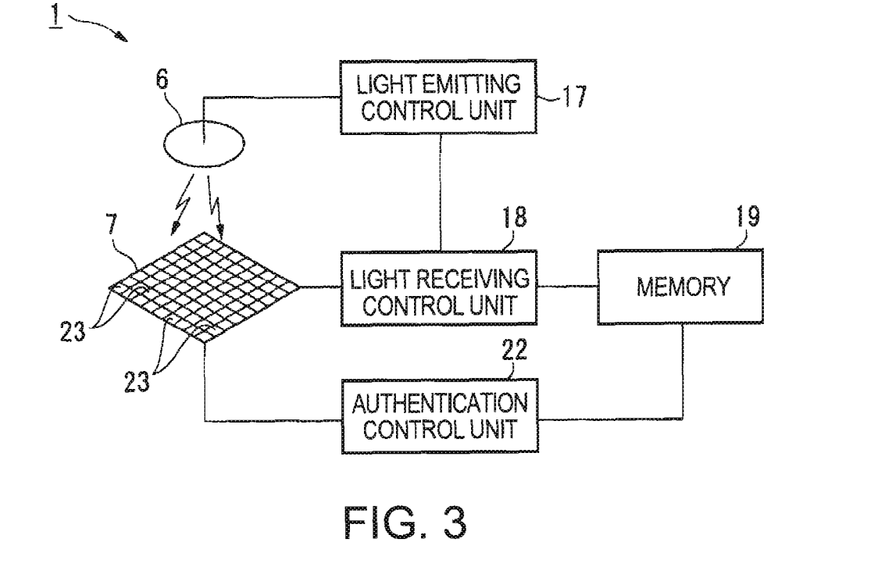
FIG. 3 is block diagram showing the biometric authentication device of FIG. 1.

The point light source unit 6 is electrically coupled to a light emitting control unit 17 as shown in FIG. 3, and emits pulsed light under control of the light emitting control unit 17.

The light receiving unit 7 includes a plurality of light receiving elements 23 arranged in arrays, and micro lens arrays (not shown) provided at the front of the plurality of light receiving elements 23.

Among the plurality of light receiving elements 23, as shown in FIG. 2, in a state where the device is worn around the wrist, one arranged in the position nearest to the point light source unit 6 is termed as a light receiving element L1, and ones arranged distant therefrom are termed as light receiving elements L2, L3 . . . as they are distant from the light receiving element L1, and one arranged at the farthest position from the point light source unit 6 is termed as a light receiving element Ln.

The plurality of light receiving elements 23 are provided with openable and closable gates (not shown).

The light receiving unit 7 is electrically coupled to a light-receiving control unit (opening and closing control unit) 18 that controls opening and closing of gates.

The light-receiving control unit 18 is coupled to a light emitting control unit 17 and a memory (biometric data storing unit) 19.

Stored in the memory 19 is a time table for making light intensities uniform among light receiving elements, as described later, based on a function representing the relationship between light intensity and time of light emitted from the point light source unit 6.

The memory 19 stores electrical signals from the light receiving unit 7 as vein pattern stored data.

The light receiving unit 7 is also electrically coupled to an authentication control unit 22 that performs personal authentication.

The authentication control unit 22 compares the vein pattern acquired data that are obtained from an electrical signal sent from the light receiving unit 7 with the vein pattern stored data that are stored in advance in the memory 19.

If the both data match, the authentication control unit 22 outputs a permission signal representing that the authentication has been completed so as to permit use of an external device.

Next, functions of the biometric authentication device 1 in the present embodiment configured as described above will be described.

First, a vein pattern of a legitimate user is registered by a legitimate user of an external device.

That is, as shown in FIG. 2, the biometric authentication device 1 is worn around the wrist such that the light receiving unit 7 is arranged inside the wrist, and the point light source unit 6 is arranged outside the wrist.

Then, a pulsed signal is input from the light emitting control unit 17 to the point light source unit 6.

Emitted from the point light source unit 6 is pulsed light.

Figure 4A:
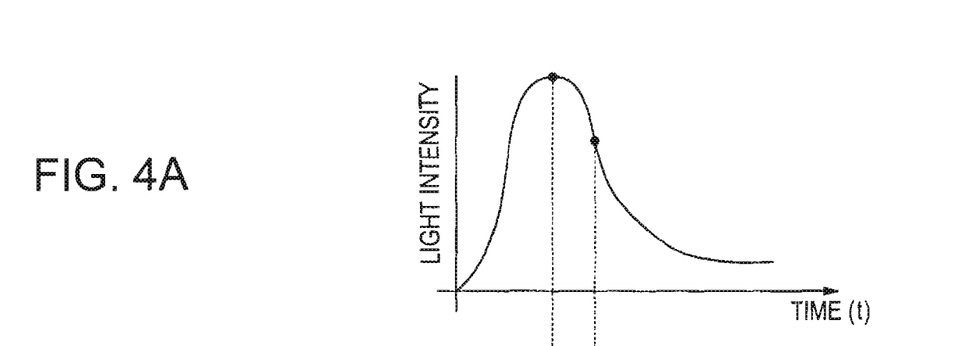
FIG. 4A is a graph showing a light intensity characteristic of light from a light source unit.

FIG. 4A is a graph showing light intensity characteristic of pulsed light at, that time.

The pulsed light is a function expressed by the following equation:

$$F(t)=A(1-e^{2t})$$

That is, the intensity of light generated in the point light source unit 6 varies with time.

The light intensity achieves a peak P after a predetermined time period has passed since the initial time, and decays after passing through the peak P.

The pulsed light is transmitted through the wrist to become transmitted light, and the transmitted light is received by the light receiving unit 7.

Here, in related art examples, if the device itself is reduced in size, the accuracy of acquired biometric data is low due to small dynamic range from the point light source unit 6, so that authentication accuracy cannot be improved.

In the invention, the accuracy of acquired biometric data can be improved by the following way.

Specifically, the light emitting control unit 17 inputs a pulsed signal to the point light source unit 6 while simultaneously inputting a light receiving direction signal to the light-receiving control unit 18.

Then, the light-receiving control unit 18 refers to a time table stored in the memory 19 and controls the timing at which a gate is opened or closed.

Figure 4B:
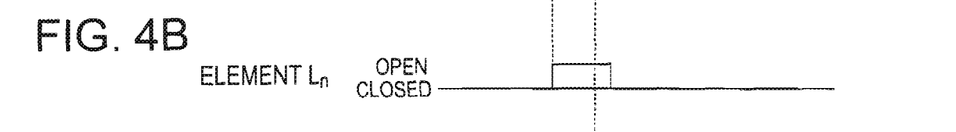
FIG. 4B is a timing chart showing the time at which the gate of a light emitting element placed remote from the light source unit is opened.
Figure 4C:
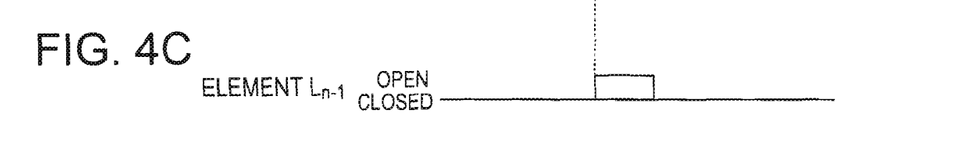
FIG. 4C is a timing chart showing the time at which the gate of a light emitting element placed near the light source unit is opened.

That is, as shown in FIGS. 4B and 4C, the light-receiving control unit 18 opens a gate for the light receiving element Ln, which is arranged at the farthest position from the point light source unit 6 when the pulsed light is at the peak P.

The timing at which the gate is opened will be termed "open time".

Further, as time has elapsed since the peak time P, the open time of the gate of each of the light receiving elements Ln-1, Ln-2, . . . , L1 is shifted sequentially toward the light receiving element L1 arranged at the nearest position to the point light source unit 6.

Therefore, the light intensities received by the light receiving elements 23 are averaged to be even (constant) regardless of the positions of the light receiving elements 23.

Thus, biometric data with high accuracy can be acquired.

Further, an electrical signal output from the light receiving unit 7 is stored as vein pattern stored data in the memory 19.

Thus, the vein pattern stored data of a legitimate user is registered.

Note that all the open times of the light receiving elements 23 are the same.

Next, authentication will be described.

In authentication, the biometric authentication device 1 is worn around the wrist to acquire a vein pattern as described above.

The authentication control unit 22 compares the vein pattern authentication data obtained from an electrical signal that is output from the light receiving unit 7 with the vein pattern stored data, that is stored in advance in the memory 19.

If the authentication control unit 22 determines that both data match, the unit outputs a permission signal representing that authentication of a legitimate user has been completed so as to permit use of an external device.

In contrast, if the authentication control unit 22 determines that both data do not match, the unit outputs a non-permission signal representing that authentication has failed.

As described above, according to the biometric authentication device 1 of the embodiment, light intensities of light received by the plurality of light receiving elements 23 can be made uniform, and therefore the light intensities can be equalized over the plurality of light receiving elements 23 regardless of their distances from the point light source unit 6.

The quality of acquired vein pattern information can be improved while the dynamic range is being decreased.

Thus, authentication accuracy can be improved.

Since the biometric authentication device 1 can be worn around the wrist, biometric authentication can be performed in various situations.

This can improve convenience.

Since pulsed light is transmitted and received, the vertical distribution of a living body can be seen without limits in the depth direction of the living body.

Note that although the open time of the gate of each of the light receiving elements 23 is shifted sequentially in the embodiment, instead of this, the gate may be controlled as follows.

Figure 5A:
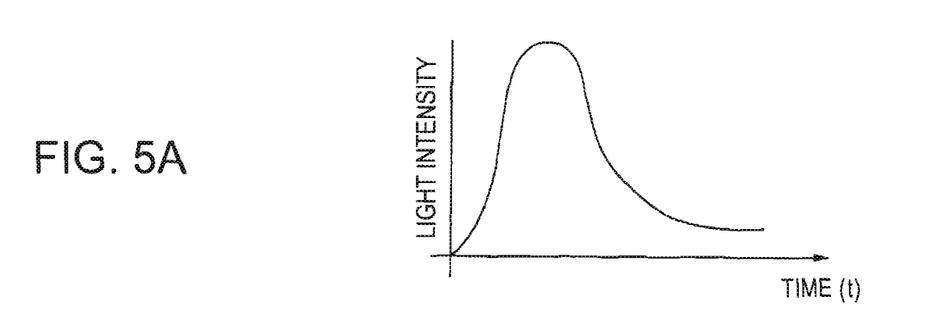
FIG. 5A is a graph showing a light intensity characteristic of light from the light source unit.

The open time of the gate of each of the light receiving elements 23 is the same for the pulsed light shown in FIG. 5A.

Figure 5B:
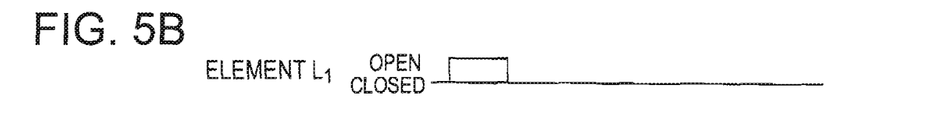
FIG. 5B is a timing chart showing a time period during which the gate of a light emitting element placed near the light source unit is opened.
Figure 5C:
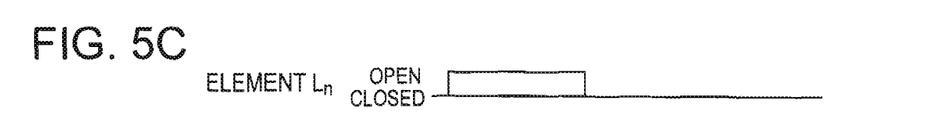
FIG. 5C is a timing chart showing a time period during which the gate of a light emitting element placed remote from the light source unit is opened.

However, the time period during which the gate of the light receiving element L1 arranged at the position near the point light source unit 6 is opened is set to be short, and the time period during which the gate is opened is subsequently made longer as the element is remote from the point light source unit 6.

Thus, intensities of light received from the light receiving unit 7 can be made uniform.

Second Embodiment

Next, a second embodiment of the invention will be described.

Figure 6:
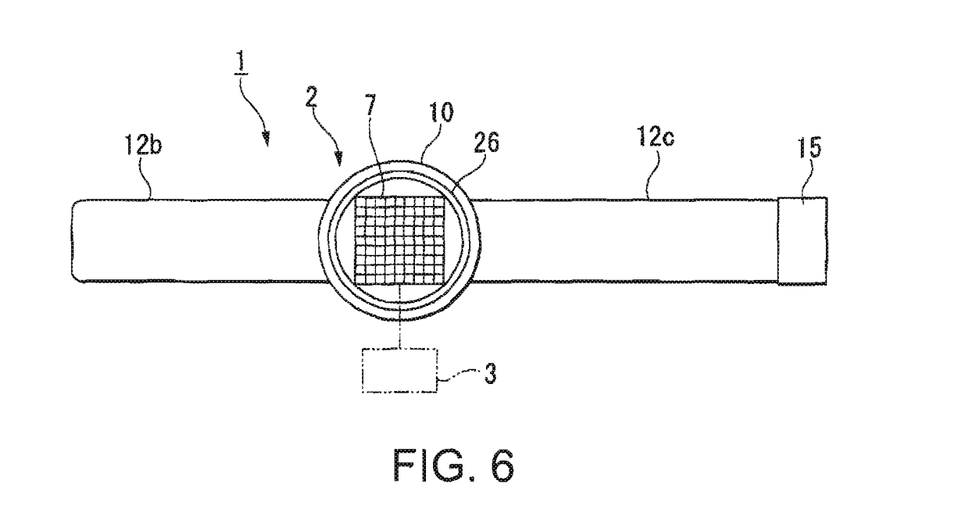
FIG. 6 is a plan view showing a second embodiment of the biometric authentication device according to the invention.
Figure 7:
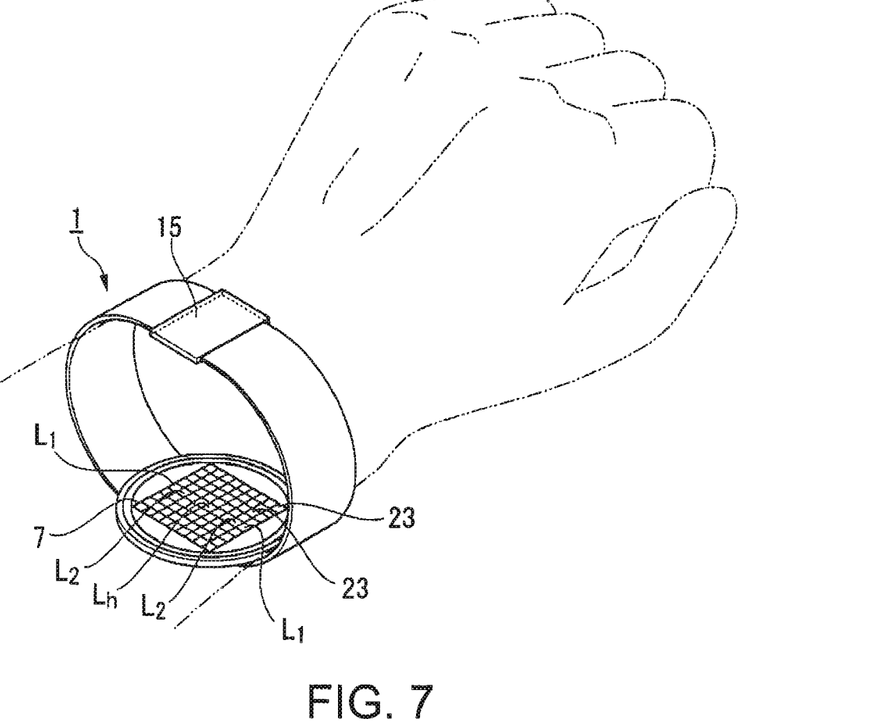
FIG. 7 is an explanatory view showing a state of the biometric authentication device of FIG. 6 worn around a wrist.

FIGS. 6 and 7 show the second embodiment of the invention.

Figure 9:
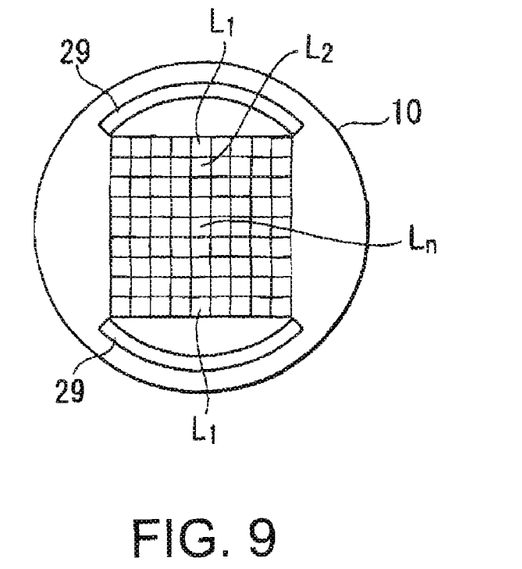
FIG. 9 is a plan view showing another modification of the light source unit of FIG. 6.

In FIGS. 6 and 7, elements that are the same as those illustrated in FIGS. 1 and 9 are indicated by the same reference numerals, and their descriptions will not be repeated.

This embodiment has the same basic structure as in the above first embodiment, and descriptions will be given on the points of difference here.

The biometric authentication device 1 in the embodiment is provided with a circular light source unit (light source unit) 26 that are formed circularly around the light receiving unit 7 as shown in FIG. 6.

Note that the rectangular base unit 11 as in the first embodiment is not provided.

The circular light source unit 26 is provided so as to surround the periphery of the light receiving unit 7.

Therefore, as shown in FIG. 7, among the plurality of light receiving elements 23, one that is arranged at the nearest position to the circular light source unit 26 is the light receiving element L1 arranged in an outer end of the light receiving unit 7, and one that is arranged at the remotest position from the circular light source unit 26 is the light receiving element Ln arranged at the center of the light receiving unit 7.

In such a structure, pulsed light is applied from the circular light source unit 26 to a wrist, the light reflects in the wrist to be reflected light, this reflected light is received by the light receiving unit 7.

As described above, gates are subsequently opened from the light receiving element Ln to the light receiving element L1.

Thus, the same effects as in the above first embodiment can be achieved.

Since reflected light from a living body is received, positions of the circular light source unit 26 and the light receiving unit 7 can be fixed.

Thus, a vein pattern can be acquired promptly and securely.

The circular light source unit 26 is provided in the embodiment.

However, a light source unit is not limited to this, and the shape and the setting location of the light source unit may be suitably changed.

Figure 8:
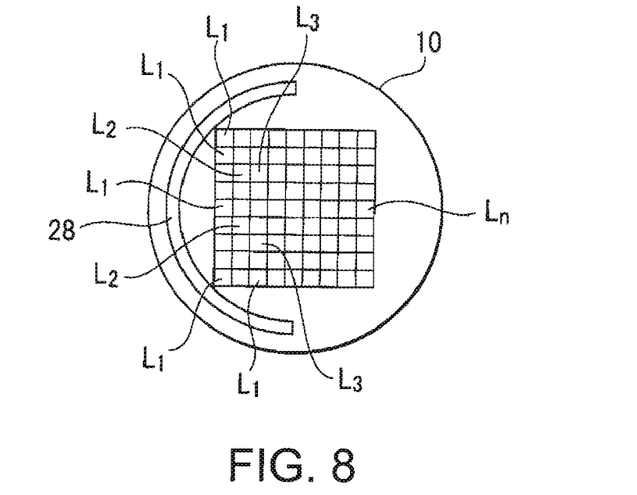
FIG. 8 is a plan view showing a modification of the light source unit of FIG. 6.

For example, as shown in FIG. 8, a semicircular light source unit (light source unit) 28 may be provided on a half of the periphery of the light receiving unit 7.

Also, as shown in FIG. 9, arc-shaped light source units (light source unit) 29 may be partially provided on the periphery of the light receiving unit 7.

Figure 10:
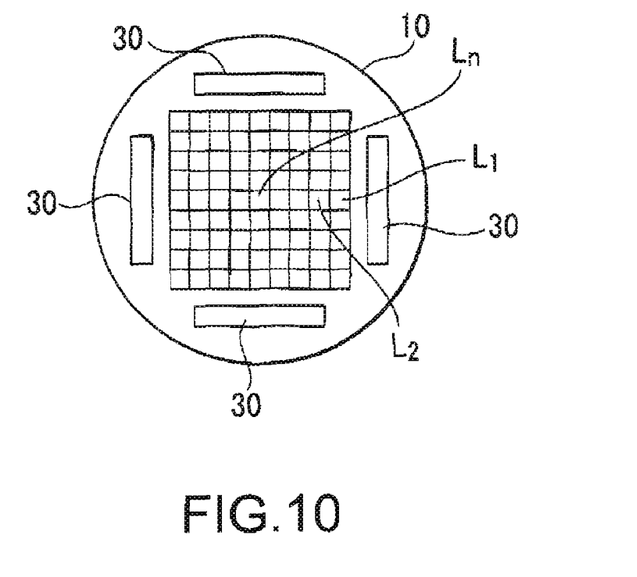
FIG. 10 is a plan view showing a still another modification of the light source unit of FIG. 6.

Further, as shown in FIG. 10, linear light source units (light source unit) 30 may be partially provided on the periphery of the light receiving unit 7.

Additionally, these light source units 26, 28, 29 and 30, instead of the point light source unit 6 of the first embodiment, may be provided in the rectangular base unit 11.

Third Embodiment

Next, a third embodiment of the invention will be described.

Figure 11:
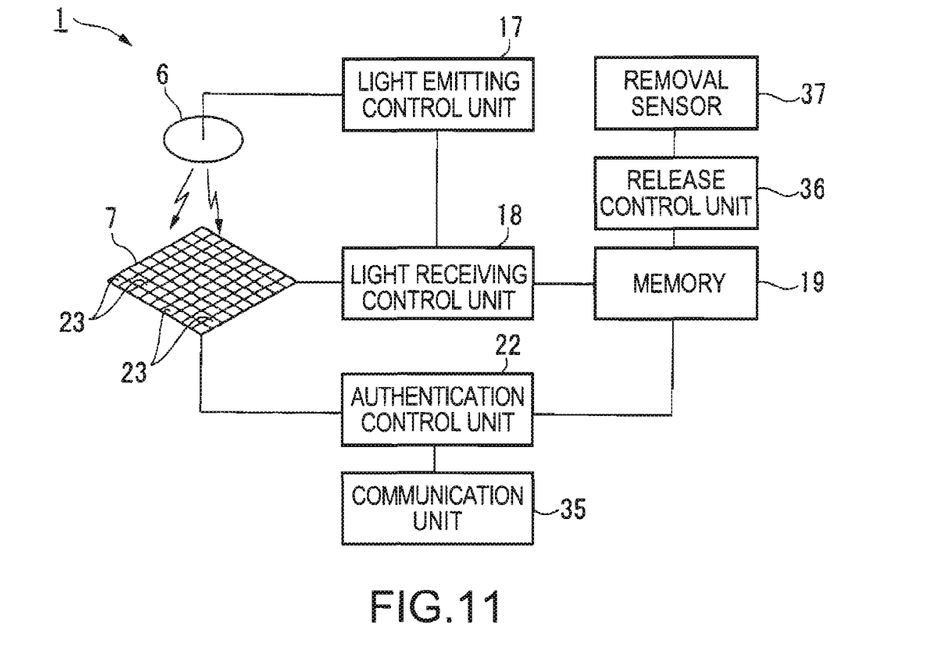
FIG. 11 is a block diagram showing a third embodiment of the biometric authentication device according to the invention for each function.

FIG. 11 shows the third embodiment of the invention.

This embodiment has the same basic structure as in the above first embodiment, and descriptions will be given on the points of difference here.

In the embodiment, coupled to the authentication control unit 22 is a communication unit (sending unit) 35 that performs communication with an external device.

Stored in the memory 19 is user identification data (ID) of a legitimate user.

The memory 19 is coupled to a removal sensor through a release control unit (release unit) 36.

Note that the memory 19 in the embodiment functions as a biometric data storing unit, an identification data storing unit and an authentication holding unit.

In such a structure, a vein pattern is acquired using the same way as described above, and if determining that vein pattern authentication data and vein pattern stored data stored in the memory 19 match, the authentication control unit 22 turns on an authentication completion flag (authentication completion information) that indicates a state in which authentication has completed.

Note that the authentication completion flag is stored in the memory 19.

Then, the authentication control unit 22 sends a permission signal by radio through a communication unit 35 to an external device.

After completion of authentication in this way, if the authentication completion flag in the memory 19 is on, the authentication control unit 22 reads out user ID in the memory 19 and sends it through the communication unit 35 to an external device.

On the other hand, when the biometric authentication device 1 is removed, a state in which the device is removed is detected by a removal sensor 37.

Then, the removal sensor 37 inputs a release direction signal to a release control unit 36, and the release control unit 36 turns off the authentication completion flag in the memory 19.

As described above, according to the biometric authentication device 1 in the embodiment, the state of completion of authentication can be held.

Therefore, as long as the biometric authentication device 1 is worn, authentication needs not be performed in each time.

This allows quick responses only with on-off determination of the authentication completion flag.

Also, if the biometric authentication device 1 is removed from a body, the state in which authentication has been completed is released.

This can improve security.

Further, when authentication is completed, user ID is sent.

This allows a coupled external device to perform various controls appropriate for each individual.

For example, controls can be performed so that when a legitimate user approaches his or her vehicle, the door lock of the vehicle is automatically released, and when the legitimate user approaches a TV at a scheduled time, the channel that is registered in advance is automatically turned on.

Fourth Embodiment

Next, a fourth embodiment of the invention will be described.

Figure 12:
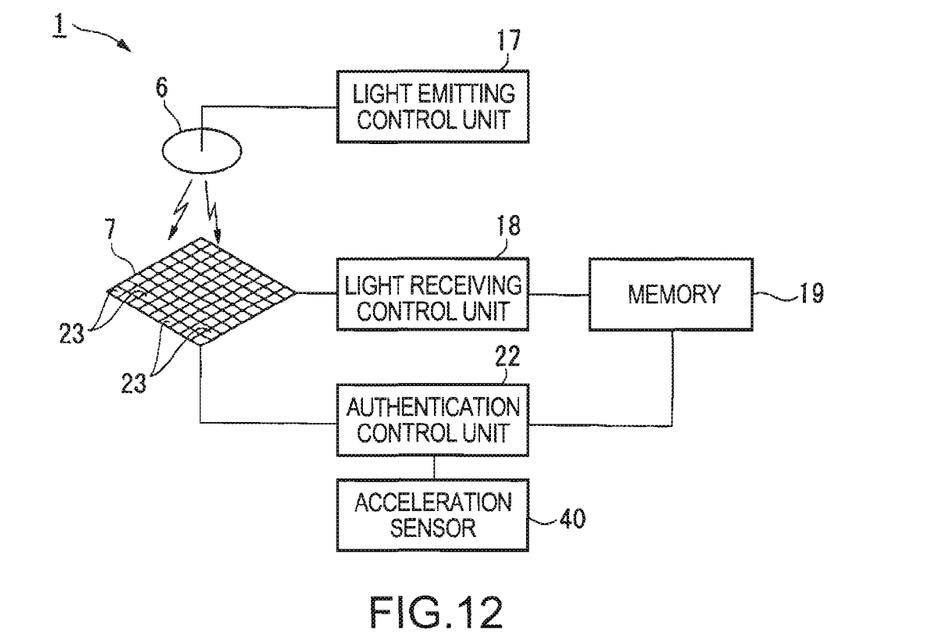
FIG. 12 is a block diagram showing a fourth embodiment of the biometric authentication device according to the invention for each function.

FIG. 12 shows the fourth embodiment of the invention.

This embodiment has the same basic structure as in the above first embodiment, and descriptions will be given on the points of difference here.

In the embodiment, an acceleration sensor (resting state detection unit) 40 that detects a motion (acceleration) of a living body is provided, and the acceleration sensor 40 is coupled to the authentication control unit 22.

In such a structure, the authentication control unit 22 compares a detected result of the acceleration sensor 40 with a predetermined threshold value that is set in advance.

If it is determined that the detected result of the acceleration sensor 40 is smaller than the predetermined threshold value, a vein pattern is acquired and personal authentication is performed in the same way as described above.

On the other hand, if it is determined that the detected result of the acceleration sensor 40 is larger than the predetermined threshold value, personal authentication is not performed.

In other words, the authentication control unit 22 functions as an authentication prohibition control unit.

As described above, according to the biometric authentication device 1 in the embodiment, the motion of a living body that represents the resting state of the living body is detected, and authentication is controlled based on the detected result.

Therefore, authentication can be performed by securely acquiring a vein pattern of the resting state of a living body.

This can improve authentication accuracy.

Note that a motion (acceleration) as the resting state of a living body is detected in the embodiment; however, the motion is not limited to this, and may be suitably changed.

In the above first to fourth embodiments, a vein pattern is acquired as biometric data.

However, this is not restrictive, and other biometric data such as fingerprint and iris may be acquired.

A light source unit is made of an LED in the embodiments; however, the light source unit is not limited to this, and may be made of an organic electroluminescence (EL), an inorganic EL or the like.

A time table is stored in the memory 19 in the embodiments.

However, this is not restrictive, and a function for calculating the inverse number of pulsed light and so on to make uniform light intensities of the received light may be stored.

Further, biometric data may be acquired a plurality of times in one authentication, and then light intensities of results are added.

As a result, noise, errors and the like can be accommodated.

Thus, biometric data can be acquired with higher accuracy.

Alternatively, when pulsed light is emitted from a light source unit at the first time, a peak intensity of pulsed light is measured, and when pulsed light is emitted at the second time, the timing of opening a gate may be controlled in accordance with the measured peak light intensity.

Additionally, in the first light emission, the amount of transmitted light or reflected light is measured, and output from the light emitting control unit 17 may be controlled depending on whether or not the light amount is within a predetermined range.

That is, feedback is performed to increase output from the light emitting control unit 17 if the light amount is smaller, or to decrease the output if the light amount is larger.

The control of output is performed using current or voltage applied to the light source unit.

This allows not only acquiring biometric data with high accuracy and reliability but also power-saving.

It is to be understood that the technical range of the invention is not limited to the above embodiments, and various changes can be made without departing from the scope and spirit of the invention.

What is claimed is:

1. A biometric data acquisition device for acquiring data of a living body by irradiating the living body with light, comprising:
    a light source unit emitting light to the living body, an intensity of the light from the light source unit being defined by a curve expressed by a predetermined formula, the curve being a function of time;
    a plurality of light receiving elements receiving one of transmitted light and reflected light, the transmitted light and the reflected light being transmitted through the living body and reflecting from the living body, respectively, by irradiating the living body with the light from the light source unit;
    an openable and closable gate provided for each of the plurality of light receiving elements; and
    an opening and closing control unit controlling opening and closing of the gate so as to make uniform an intensity of light received by the plurality of light receiving elements, a timing of the opening and closing of the gate being controlled based on the intensity of the light from the light source unit and a distance between the light source unit and each of the plurality of light receiving elements.

2. The biometric data acquisition device according to claim 1, wherein the opening and closing control unit sets a time to open a gate corresponding to one of the plurality of light receiving elements arranged in a position remote from the light source unit in accordance with a time at which an intensity of light emitted from the light source unit is high, and sets a time to open a gate corresponding to one of the plurality of light receiving elements arranged in a position near to the light source unit in accordance with a time at which the intensity is low.

3. The biometric data acquisition device according to claim 2, wherein a time to open a gate corresponding to one of the light receiving elements arranged in a position remotest from the light source unit is set in accordance with a time at which an intensity of light emitted from the light source unit is at a peak, and as, starting from the one of the light receiving elements arranged in a position remotest from the light source unit, each light receiving element is nearer to the light source unit, a time to open the gate is subsequently shifted in accordance with decay of the intensity of the light.

4. The biometric data acquisition device according to claim 1, wherein the opening and closing control unit makes long a time period during which a gate corresponding to one of the plurality of light receiving elements arranged in a position remote from the light source unit is opened, and makes short a time period during which a gate corresponding to one of the plurality of light receiving elements arranged in a position near to the light source unit is opened.

5. The biometric data acquisition device according to claim 1, wherein the biometric data acquisition device is wearable on a body.

6. A biometric data acquisition method for acquiring data of a living body by irradiating the living body with light, comprising:
    irradiating the living body with light emitted from a light source unit, an intensity of the light from the light source unit being defined by a curve expressed by a predetermined formula, the curve being a function of time;

receiving one of transmitted light and reflected light by a plurality of light receiving elements, the transmitted light and the reflected light being transmitted through the living body and reflecting from the living body, respectively, by irradiating the living body with the light from the light source unit; and making uniform an intensity of light received by the plurality of light receiving elements by an opening and closing control unit controlling opening and closing of a gate provided for the plurality of light receiving elements, a timing of the opening and closing of the gate being controlled based on the intensity of the light from the light source unit and a distance between the light source unit and each of the plurality of light receiving elements.

7. A biometric authentication device, comprising:

a biometric data acquisition unit for acquiring data of a living body by irradiating the living body with light; and an authentication unit for performing personal authentication with the data of the living body acquired by the biometric data acquisition unit;

the biometric data acquisition unit, including:

a light source unit emitting light to the living body, an intensity of the light from the light source unit being defined by a curve expressed by a predetermined formula, the curve being a function of time;

a plurality of light receiving elements receiving one of transmitted light and reflected light, the transmitted light and the reflected light being transmitted through the living body and reflecting from the living body, respectively, by irradiating the living body with the light from the light source unit;

an openable and closable gate provided for each of the plurality of light receiving elements; and an opening and closing control unit controlling opening and closing of the gate so as to make uniform an intensity of light received by the plurality of light receiving elements, a timing of the opening and closing of the gate being controlled based on the intensity of the light from the light source unit and a distance between the light source unit and each of the plurality of light receiving elements;

the authentication unit, including:

a biometric data storing unit storing in advance data of the living body acquired by the biometric data acquisition unit; and an authentication control unit comparing the data of the living body stored in advance in the biometric data storing unit with the data of the living body acquired in authentication by the biometric data acquisition unit, and if both the stored data and the acquired data match, outputting a permission signal representing completion of authentication.

8. The biometric authentication device according to claim 7, wherein the biometric authentication device is wearable on a body.

9. A biometric authentication device, comprising:

a biometric data acquisition unit for acquiring data of a living body by irradiating the living body with light; and an authentication unit for performing personal authentication with the data of the living body acquired by the biometric data acquisition unit;

the biometric authentication device being coupled to an external device, and being designed to be wearable on a body;

the biometric data acquisition unit, including:

a light source unit emitting light to the living body, an intensity of the light from the light source unit being defined by a curve expressed by a predetermined formula, the curve being a function of time;

a plurality of light receiving elements receiving one of transmitted light and reflected light, the transmitted light and the reflected light being transmitted through the living body and reflecting from the living body, respectively, by irradiating the living body with the light from the light source unit;

an openable and closable gate provided for each of the plurality of light receiving elements; and an opening and closing control unit controlling opening and closing of the gate so as to make uniform an intensity of light received by the plurality of light receiving elements, a timing of the opening and closing of the gate being controlled based on the intensity of the light from the light source unit and a distance between the light source unit and each of the plurality of light receiving elements;

the authentication unit, including:

a biometric data storing unit storing in advance data of the living body acquired by the biometric data acquisition unit;

an identification data storing unit storing identification data of an individual;

an authentication control unit comparing the data of the living body stored in advance in the biometric data storing unit with the data of the living body acquired in authentication by the biometric data acquisition unit, and if both the stored data and the acquired data match, outputting a permission signal representing completion of authentication.

an authentication holding unit holding authentication completion information indicating a state of completed authentication;

a release unit releasing a state of the authentication completion information held by the authentication holding unit when detecting the biometric authentication device is removed from the body; and a sending unit sending identification data stored in the identification data storing unit to the external device when a permission signal output from the authentication control unit is input.

10. A biometric authentication device, comprising:

a biometric data acquisition unit for acquiring data of a living body by irradiating the living body with light; and an authentication unit for performing personal authentication with the data of the living body acquired by the biometric data acquisition unit;

the biometric data acquisition unit, including:

a light source unit emitting light to the living body, an intensity of the light from the light source unit being defined by a curve expressed by a predetermined formula, the curve being a function of time;

a plurality of light receiving elements receiving one of transmitted light and reflected light, the transmitted light and the reflected light being transmitted through the living body and reflecting from the living body, respectively, by irradiating the living body with the light from the light source unit;

an openable and closable gate provided for each of the plurality of light receiving elements; and an opening and closing control unit controlling opening and closing of the gate so as to make uniform an intensity of light received by the plurality of light receiving elements, a timing of the opening and closing of the gate being controlled based on the intensity of the light from the light source unit and a distance between the light source unit and each of the plurality of light receiving elements;

the authentication unit, including:

a resting state detection unit detecting a resting state of the living body;

a biometric data storing unit storing in advance a vein pattern of the living body acquired by the biometric data acquisition unit;

an authentication control unit comparing the vein pattern stored in advance in the biometric data storing unit with the vein pattern acquired in authentication by the biometric data acquisition unit, and if both the stored vein pattern and the acquired vein pattern match, outputting a permission signal representing completion of authentication; and an authentication prohibition control unit prohibiting authentication by the authentication control unit if a result detected by the resting state detection unit exceeds a predetermined threshold value.

11. A biometric data acquisition device for acquiring data of a living body by irradiating the living body with light, comprising:

a light source unit emitting light to the living body, an intensity of the light from the light source unit being defined by a curve expressed by a predetermined formula, the curve being a function of time;

a plurality of light receiving elements receiving one of transmitted light and reflected light, the transmitted light and the reflected light being transmitted through the living body and reflecting from the living body, respectively, by irradiating the living body with the light from the light source unit; and a plurality of openable and closable gates, the plurality of gates each provided for one of the plurality of light receiving elements, at least two of the plurality of gates being opened at a different timing after starting irradiation of the living body with the light, a timing of the opening and closing of each of the plurality of gates being controlled based on the intensity of the light from the light source unit and a distance between the light source unit and a respective one of the plurality of light receiving elements.

12. A biometric data acquisition device for acquiring data of a living body by irradiating the living body with light, comprising:

a light source unit emitting light to the living body, an intensity of the light from the light source unit being defined by a curve expressed by a predetermined formula, the curve being a function of time;

a plurality of light receiving elements receiving one of transmitted light and reflected light, the transmitted light and the reflected light being transmitted through the living body and reflecting from the living body, respectively, by irradiating the living body with the light from the light source unit; and a plurality of openable and closable gates, the plurality of gates each provided for one of the plurality of light receiving elements, at least two of the plurality of gates being closed at a different timing after the at least two gates having been opened, a timing of the opening and closing of each of the plurality of gates being controlled based on the intensity of the light from the light source unit and a distance between the light source unit and a respective one of the plurality of light receiving elements.

13. The biometric data acquisition device according to claim 11, wherein an intensity of the light varies with time.

14. The biometric data acquisition device according to claim 1, wherein the emitted light from the light source unit is unfiltered pulsed light, the unfiltered pulsed light is defined by the predetermined formula, and an intensity of the unfiltered pulsed light emitted from the light source unit varies with time.

15. The biometric data acquisition method according to claim 6, wherein the light emitted from the light source unit is unfiltered pulsed light, the unfiltered pulsed light is defined by the predetermined formula, and an intensity of the unfiltered pulsed light emitted from the light source unit varies with time.

16. The biometric data acquisition device according to claim 2, wherein the opening and closing control unit sets an exposure time relating to the total time a gate corresponding to one of the plurality of light receiving elements remains open, and the exposure time being the same for each of the plurality of light receiving elements, regardless of the remoteness of the light receiving elements from the light source unit.

17. The biometric data acquisition device according to claim 1, wherein the light source unit is chosen from the group consisting of an LED, organic electroluminescence, or inorganic electroluminescence.

18. The biometric data acquisition device according to claim 1, wherein the plurality of light receiving elements receive the transmitted light transmitted through the living body.

19. The biometric data acquisition device according to claim 1, wherein the predetermined formula is $F(t)=A(1-e^{-2t})$, where $F(t)$ represents the intensity of the light from the light source unit as a function of time, A represents a scaling constant, e represents Euler's number, and t represents time.

* * * * *